(12) United States Patent
Li et al.

(10) Patent No.: US 8,456,640 B2
(45) Date of Patent: Jun. 4, 2013

(54) APPARATUS AND METHOD FOR MEASURING REFLECTANCE OF OPTICAL LASER COMPONENTS

(75) Inventors: Bincheng Li, Chengdu (CN); Zhechao Qu, Chengdu (CN); Yanling Han, Chengdu (CN)

(73) Assignee: Institute of Microelectronics, Chinese Academy of Sciences, Beijing (CN)

( * ) Notice: Subject to any disclaimer, the term of this patent is extended or adjusted under 35 U.S.C. 154(b) by 119 days.

(21) Appl. No.: 13/231,711

(22) Filed: Sep. 13, 2011

(65) Prior Publication Data

US 2012/0154815 A1 Jun. 21, 2012

(51) Int. Cl.
 *G01N 21/00* (2006.01)
 *G01N 21/55* (2006.01)

(52) U.S. Cl.
 CPC ........................................ *G01N 21/55* (2013.01)
 USPC ........................................................ 356/445

(58) Field of Classification Search
 CPC ..................................................... G01N 21/55
 USPC .................................................. 356/445–448
 IPC ..................................................... G01N 21/55
 See application file for complete search history.

(56) References Cited

U.S. PATENT DOCUMENTS 5,903,358 A * 5/1999 Zare et al. ..................... 356/437
7,679,750 B2 * 3/2010 Li et al. .......................... 356/445

FOREIGN PATENT DOCUMENTS

| CN | 1242516 A | 1/2000 |
|---|---|---|
| CN | 1804572 A | 7/2006 |
| CN | 1963435 A | 5/2007 |
| CN | 101055224 A | 10/2007 |
| CN | 101261181 A | 9/2008 |
| CN | 101261182 A | 9/2008 |

OTHER PUBLICATIONS

Virgil Sanders, High-precision reflectivity measurement technique for low-loss laser mirror, Applied Optics, Jan. 1977, vol. 16, No. 1, pp. 19-20.
Angela Duparre et al., Optical Interference Coatings 2010 Measurement Problem, Applied Optics, Mar. 20, 2011, vol. 50, No. 9, pp. C172-C177.
International Standard, ISO13697, 2006.
International Standard, ISO15368, 2001.
G. Rempe et al., Measurement of ultralow losses in an optical interferometer, Optical Society of America, Mar. 1, 1992, vol. 17, No. 5, pp. 363-365.

(Continued)

*Primary Examiner* — Michael P Stafira
(74) *Attorney, Agent, or Firm* — China Science Law Group

(57) ABSTRACT

Apparatus and methods for measuring reflectance of optical laser components are disclosed. In one embodiment, when the reflectance of the test optical laser component is higher than 98%, a cavity ring-down (CRD) technique based configuration is employed to measure the reflectance of the test optical laser component. On the other hand, when the reflectance of the test optical laser component is lower than 98% or there is no measurable CRD signal, by removing the output cavity mirror in the CRD apparatus, a photometric configuration is formed to measure the reflectance. The switching between the two techniques can be achieved by removing or inserting the output cavity mirror of the ring-down cavity in the CRD apparatus.

20 Claims, 3 Drawing Sheets

OTHER PUBLICATIONS

I. Debecker et al., High-speed cavity ringdown spectroscopy with increased spectral resolution by simultaneous laser and cavity tuning, Optics Express, Apr. 18, 2005, vol. 13, No. 8, pp. 2906-2915.

Bincheng Li et al., Review of Cavity Ring-Down Techniques for High Reflectivity Measurements, Laser & Optoelectronics Progress, 2010, pp. 021203-1 to 021203-11.

D. Romanini et al., CW cavity ring down spectroscopy, Chemical Physical Letters, Jan. 10, 1997, pp. 316-322.

Anthony O'Keefe et al., Cavity ring-down optical spectrometer for absorption measurements using pulsed laser sources, Rev. Sci. Instrum. 59(12), Dec. 1988, pp. 2544-2551.

A. Voss et al., Simple high-precision method for measuring the specular reflectance of optical components, Applied Optics, Dec. 20, 1994, vol. 33, No. 36, pp. 8370-8374.

English Abstract of CN98114152.8.
English Abstract of CN200610011254.9.
English Abstract of CN200610165082.0.
English Abstract of CN200710098755.X.
English Abstract of CN200810055653.4.
English Abstract of CN200810102778.8.

* cited by examiner

APPARATUS AND METHOD FOR MEASURING REFLECTANCE OF OPTICAL LASER COMPONENTS

CROSS-REFERENCE TO RELATED APPLICATION(S)

This application claims priority to Chinese Application No. 201010608932.6, filed on Dec. 17, 2010, the disclosure of which is incorporated herein by reference in its entirety.

TECHNICAL FIELD

The technology relates generally to apparatus and methods for measuring reflectance of optical laser components.

BACKGROUND

Optical coatings often play a crucial role in the performance of optical instruments. Traditional techniques for reflectance measurement, which are based on spectrophotometry (ISO 15368) or ratiometry (ISO 13697), have an accuracy limitation of around 0.01%, due to the intensity fluctuation of light sources used. It is difficult to determine reliably a high reflectance (R>99.9%) using conventional instruments and methods.

Several experimental setups for direct measurement of specular reflectance with single, double, and multiple reflection configurations were developed in the past. The measurement accuracy generally increases with the number of reflections, but the high complexity of setups based on multiple reflection causes undesired restrictions, and their high sensitivity to optical misalignment is an additional error source.

To measure the reflectance approaching unity, the so-called cavity ring-down (CRD) method has been developed. CRD technique is a highly sensitive and unique technique for measuring the reflectance of highly-reflective (HR) coatings. In CRD setups, a laser beam is injected into a high-finesse optical resonator, called as a ring-down cavity (RDC). When the light source is abruptly terminated, light trapped inside the RDC decays due to finite resonator losses and can be monitored by detecting the power of light transmitted through a mirror of the RDC. Typically, the light exiting the RDC decays exponentially in time domain with a characteristic decay time, called as a ring-down decay time. The rate of decay is directly proportional to cavity losses due to transmission, scattering, diffraction, absorption etc.

The CRD technique has the advantages of (1) insensitivity to the power fluctuation of the light source over the conventional spectrophotometric and ratiometric methods and (2) the increased reflectance measurement accuracy with the increasing reflectance of the test component. The results of a recent round robin measurement of reflectance [Appl. Opt. 50(9): C172-C177 (2011)] indicate clearly that when R>99.99%, the reflectance can be accurately measured only by CRD equipment, and for R>99%, the measurement accuracy with the CRD equipment is much superior to other spectrophotometry or ratiometry based instruments.

During recent years, many CRD experimental schemes have been developed employing either a pulsed laser or a continuous-wave (CW) laser. Nowadays numerous articles and patents can be found, providing various CRD arrangements and methods. For detailed information, references can be made to, for example, the articles by O'Keefe and Deacon in Rev. Sci. Instrum. 59(12): 2544-2551 (1988), Romanini et al. in Chem. Phys. Lett. 264: 316-322 (1997) and U.S. Pat. Nos. 6,839,140 and 6,466,322.

On the other hand, for a typical CRD instrument, the measurement accuracy for 98% reflectance is in the range of 0.1%-0.5%, which is comparable to that of the photometric technique. As the reflectance of the test component decreases, the measurement error of the reflectance with the CRD technique increases, that is, $\Delta R/R=(1-R)(\Delta L/L+\Delta\tau/\tau)$ where R denotes the reflectance, L denotes the RDC length and $\tau$ denotes the decay time. Therefore there is no advantage to use CRD technique to measure a reflectance lower than 98%. In addition, when the reflectance is lower than 95%, it is difficult to be measured by the CRD technique. In this case, the traditional spectrophotometry or ratiometry based technique should be used for measuring the reflectance lower than 98%. Consequently, an apparatus integrating both CRD technique and the photometric technique is able to measure the reflectance of optical laser components in the range of 0 to 99.9999% or more, and with an improved accuracy when the reflectance is higher than 98%.

A technique for measuring reflectance suggested by Virgil Sanders, Appl. Opt. 16(1): 19-20 (1977) works well for optical elements with moderate losses defined as 1-R, but less so when losses become very low. The proposed technique measures the total reflection loss of polarized light using two intralaser cavity measurements, one with the test component and one without, by varying the angle of a rotatable window in the path of the beam in the cavity from Brewster's angle until the laser action was quenched in both directions. The difference in the angle of incidence for the two measurements is a measure of the total loss in the test component with this method. It is difficult to determine high reflectance (R>99.9%) with a desirable accuracy.

A. Voss et al. have proposed a method to determine precisely the specular reflectance of optical components [Appl. Opt. 33(36): 8370-8374 (1994)]. A laser with high temporal and spatial stability is employed. An optically flat and highly reflective chopper mirror divides the laser beam into a probe beam and a reference beam. The application of lock-in technique with an amplifier locked to the chopper frequency permits the detection of small power levels that corresponded to small reflection losses. The detection limit is determined by the relative intensity noise of the laser source, the ratio of the noise equivalent power to the incident power of the detector.

Recently, efforts have been made to overcome most of the limitations of pulsed CRD by using narrow-band CW lasers. By coupling the CW laser into the high finesse RDC, the power of light inside the RDC is built up, and the cavity output increases. A method based on the decay time measurement for determining the ultra-low losses of an optical cavity is disclosed by G. Rempe, R. J. Thompson, H. J. Kimble in "Measurement of ultra-low losses in an optical interferometer", Opt. Lett., 17(5): 363-365 (1992). A piezoelectric transducer (PZT) is employed to slowly scan the length of the optical cavity, making the laser frequency periodically resonant with the cavity Eigen-modes. The CW laser beam is switched off by an acousto-optic switch (AOS) when the amplitude of the cavity output signal exceeds a predefined threshold and the subsequent decay of the cavity output is recorded to determine the decay time and the cavity losses. This technique enhances the efficiency of the decay time measurement, however, is relatively costly and complicated due to the use of PZT and AOS.

However, for reflectance less than 98%, the CRD technique is not an appropriate technique for reflectance measurements of the optical mirrors, as the CRD technique cannot measure reflectance lower than 95% and the measurement accuracy is only comparable to that of the spectrophotometry or ratiometry based reflectance measurement techniques when the reflectance is around 98%, and the measurement accuracy decreases with the decreasing reflectance of the laser components under test.

SUMMARY

Several embodiments of the present technology are related to apparatus and methods for accurate measurement of reflectance of optical laser components. In certain embodiments, an apparatus includes a stable Ring-Down Cavity (RDC) which comprises two plano-concave mirrors and a planar mirror. All three mirrors are highly reflective. A function generation unit provides a square-wave signal to modulate the excitation current/voltage of a CW semiconductor laser. The laser beam is split into a reference laser beam and a probe laser beam by a beam splitter. The probe laser beam is obliquely incident on the planar mirror and transmitted into the optical ring-down cavity along the optical axis of the optical ring-down cavity. A detector (the first detector) and a lens or lens set are used to measuring the power of the probe laser beam exiting the optical ring-down cavity, and transforming the laser power into an electrical signal. Another detector (the second detector) and a lens or lens set are placed in the beam path of the reference laser beam to measure the power of the reference laser beam and transform the laser power into an electrical signal. A data acquisition unit acquires the electrical signals from the first and second detectors. A computer is used for controlling the function generation unit and the data acquisition unit, and also for processing the electrical signals from the first and second detectors to determine the reflectance of the test component.

According to an aspect of the present technology, when the reflectance of the test component measured by Cavity Ring-Down (CRD) technique is lower than 98%, or when there is no measurable ring-down signal in the CRD technique, the output cavity mirror of the RDC is removed, and a photometric apparatus is formed to measure the reflectance.

According to additional aspects of the present technology, a method includes (1) providing a stable, initial optical ring-down cavity with two plano-concave mirrors and a planar mirror; (2) directing a probe laser beam into the optical cavity from the planar mirror, with the probe laser beam emitted from a semiconductor laser and transmitted through a beam splitter; (3) measuring and transforming the optical power of the probe laser beam transmitted through the optical cavity into an electrical signal by the first detector, recording the electrical signal immediately after switching off the semiconductor laser and determining the decay time of the initial optical ring-down cavity from the measured CRD signal; (4) measuring and transforming the optical power of a reference laser beam into an electrical signal by the second detector, with the reference laser beam emitted from the semiconductor laser and reflected by the beam splitter; (5) removing the output cavity mirror of the optical cavity, measuring and transforming the optical power of the probe laser beam into an electrical signal by the first detector; (6) inserting a test component into the initial optical ring-down cavity to form a test optical cavity, repeating operations (2) to (4) to determine the decay time of the test optical cavity, and measuring and transforming the optical power of the probe laser beam into an electrical signal by the first detector after removing the output cavity mirror of the test optical cavity; (7) calculating the reflectance of the test component according to decay times of the initial and test optical cavities.

When the calculated reflectance of the test component by operation (7) is lower than 98%, or when there is no measurable CRD signal in operation (6), the reflectance of the test component is calculated via calculating a ratio the electrical signal amplitudes of the first and second detectors and calibrating the ratio.

The foregoing Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION OF THE TECHNOLOGY

Various embodiments of systems, apparatus, and associated methods for measuring reflectance of optical laser components are described below. Specific examples of such systems, apparatus, and associated methods are discussed below in detail for illustration purposes. A person skilled in the relevant art will also understand that the technology may have additional embodiments, and that the technology may be practiced without several of the details of the embodiments described below with reference to FIGS. 1-3.

Figure 1:
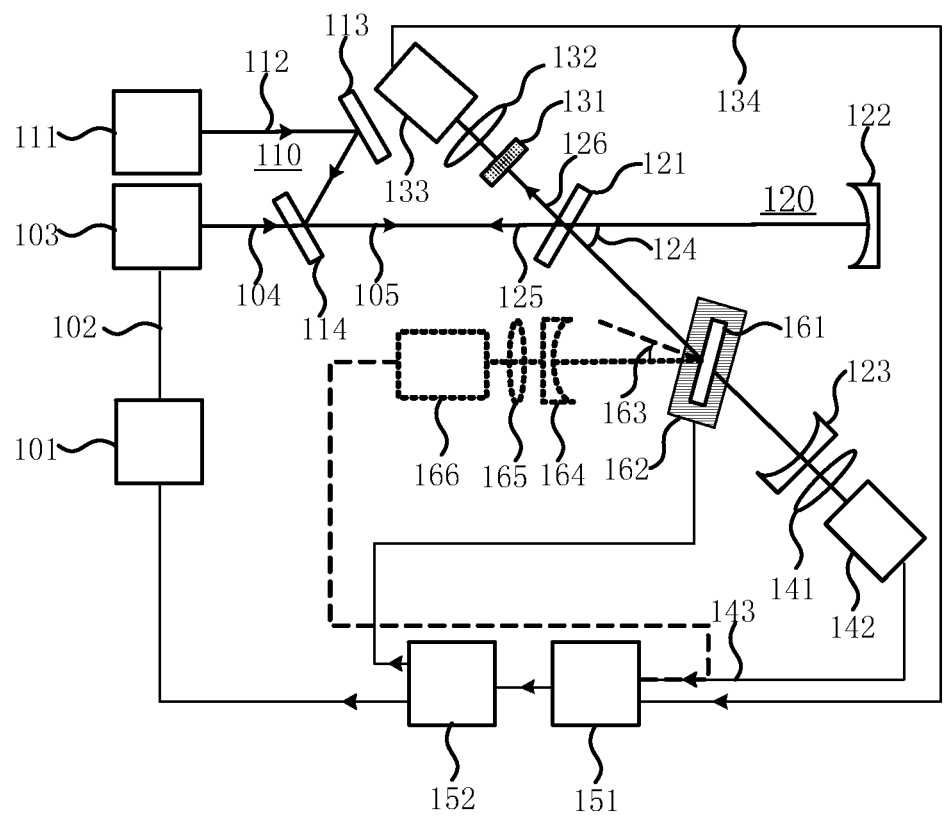
FIG. 1 is a schematic diagram of an apparatus in accordance with embodiments of the present technology.

FIG. 1 illustrates an embodiment of an apparatus in accordance with embodiments of the present technology. As shown in FIG. 1, a square-wave electrical signal 102 is generated from a function generation unit 101 and used to modulate the excitation voltage of a semiconductor laser 103. A laser beam 104, whose intensity is thus square-wave modulated, is emitted from the semiconductor laser 103. An additional channel 110 is introduced for the alignment of the laser beam 104 if the laser beam 104 is invisible.

A visible laser beam 112, generated from a light source 111, is adjusted by a reflective mirror 113 and a dichromatic beam splitter 114 to be coaxial with the laser beam 104, making it convenient to precisely adjust the optical components in the optical path of the laser beam 104. The light source 111 is switched off at the time of data acquisition for reflectance measurement. An (initial) optical cavity 120 is consist of a first plano-concave cavity mirror 122, a second plano-concave cavity mirror 123 (also the output cavity mirror) and a planar mirror 121 (also works as a beam splitter).

A combined beam 105 (the laser beam 104 transmitting the dichromatic beam splitter 114 for reflectance measurement) is split by the beam splitter 121 into two beams, that is, a probe laser beam and a reference laser beam 126. The beam splitter 121 is also one of optical cavity mirrors in order to optimize the configuration of the apparatus. However, the beam splitter can also be a separate component which is not used as the optical cavity mirror and is placed between the semiconductor laser 103 and the optical cavity 120.

The probe laser beam is obliquely incident on the planar highly-reflective (HR) mirror 121 and coupled into the initial optical cavity 120. The concave surfaces of the cavity mirrors, 122 and 123, are HR coated with a reflectance higher than 99%. The initial optical cavity 120 is an optically-stable cavity, which is defined by $0<(1-L_1/r_1)(1-L_1/r_2)<1$, with $L_1$ the on-axis cavity length of the initial optical cavity 120. $r_1$ and $r_2$ are the radii of the curvature of the concave surfaces of the optical cavity mirrors, 122 and 123, respectively. The planar mirror 121 and the first plano-concave cavity mirror 122 construct the first arm of the initial optical cavity 120, while the planar mirror 121 and the second plano-concave cavity mirror 123 construct the second arm. The angle 124 between the two arms of the initial optical cavity 120 is between about 3° to about 150° following the intended angle of incidence of the planar mirror 121. When the second plano-concave cavity mirror 123 is removed, the reference laser beam 126 includes only the direct reflection of the laser beam 105 by the planar mirror 121.

The probe laser beam exiting the initial optical cavity 120 through the second plano-concave cavity mirror 123 is focused into a photo-detector 142 (the first detector) by a lens 141. The photo-detector 142 transforms the detected laser power into an electrical signal 143, which is recorded by a data acquisition unit 151 and analyzed by a computer 152. Both the data acquisition unit 151 and the function generation unit 101 are controlled by the computer 152.

The power of the reference laser beam 126 is adjusted by a variable attenuator 131 and then focused by a lens 132 into a photo-detector 133 (the second detector) which transforms the detected laser power into an electrical signal 134. The electrical signal 134 is sent to the data acquisition unit 151 for data acquisition. For optimized measurement accuracy, the variable attenuator 131 is used for adjusting the power of the reference laser beam 126 to make the amplitudes of electrical signals 134 and 143 comparable.

A square-wave signal generated by the function generation unit 101 is used to modulate the excitation voltage of the semiconductor laser 103 to switch on and off the laser output and as a reference signal to trigger the data acquisition unit 151 to start acquiring data. The output of the semiconductor laser 103 is switched off at the negative step of each modulation period. The amplitude of the cavity output signal, also referred to as CRD signal or cavity decay signal, frequently exceeds a predefined threshold (100 mV according to the exemplary apparatus of the present technology), as shown in FIG. 1.

Figure 2:
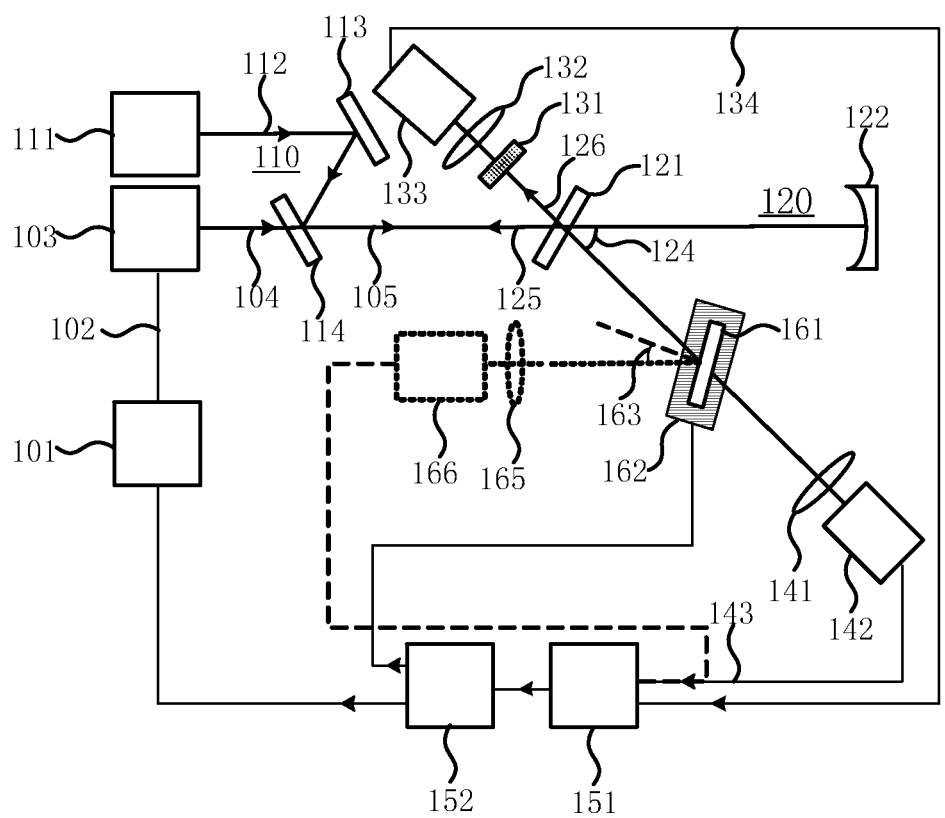
FIGS. 2 and 3 are schematic views of the photometric technique in accordance with embodiments of the present technology.

After the semiconductor laser 103 is switched off, the exponential decay of the optical cavity output signal is detected by the photo-detector 142 and fitted to an exponential decay function, $a\exp(-t/\tau_1)+b$, where a denotes the amplitude factor, b denotes the offset of the amplitude and $\tau_1$ denotes the cavity decay time, respectively. After the initial optical cavity decay time $\tau_1$ is determined, removing the second plano-concave cavity mirror 123 as shown in FIG. 2, the photo-detectors 142 and 133 simultaneously detect the power of the probe and reference laser beams, respectively. The ratio $P_1=P_{d1}/P_{r1}$ is obtained, where $P_{d1}$ and $P_{r1}$ denote the power of the probe and reference laser beams, respectively.

In order to determine the reflectance of a test optical laser component 161, the test component 161 is inserted into the second arm of the initial optical cavity 120 to form a four-mirror test optical cavity, as shown in FIG. 1 (dotted line). The second plano-concave cavity mirror 123, the photo-detector 142 and the lens 141 are moved accordingly to the position 164, 166 and 165 respectively (indicated by the second plano-concave cavity mirror 164, the photo-detector 166 and the lens 165 respectively for short). The angle of incidence 163 of the probe laser beam onto the test component 161 is set to the required testing angle of incidence of the test component.

Again, a cavity output signal is recorded at the negative step of modulation period and the exponential decay signal is fitted to an exponential decay function, $a\exp(-t/\tau_2)+b$, where a denotes the amplitude factor, b denotes the dc offset of the amplitude and $\tau_2$ denotes the cavity decay time, respectively. The test cavity decay time $\tau_2$ is determined. Thus the reflectance of the test component $R_x$ is calculated by $R_x=\exp(L_1/c\tau_1-L_2/c\tau_2)$, where $L_1$ and $L_2$ denote the on-axis cavity lengths of the initial and test optical cavities, respectively. If the calculated $R_x$ is lower than 98% or there are no measurable cavity decay signals in the test optical cavity, removing the second plano-concave cavity mirror 164 as shown in FIG. 2, the photo-detectors 166 and 133 simultaneously detect the power of the probe and reference laser beams, respectively. The ratio $P_2=P_{d2}/P_{r2}$ is obtained, where $P_{d2}$ and $P_{r2}$ denote the power of the probe and reference laser beams, respectively. The reflectance of the test component $R_x$ is calculated by $R_x=P_2/P_1$.

For reflectance mapping, the test optical laser component 161 is placed on a two-dimensional translation stage 162 which is controlled by the computer 152. By raster scanning the position of the two-dimension translation stage 162, the reflectance mapping of the test component 161 can be obtained.

Figure 3:
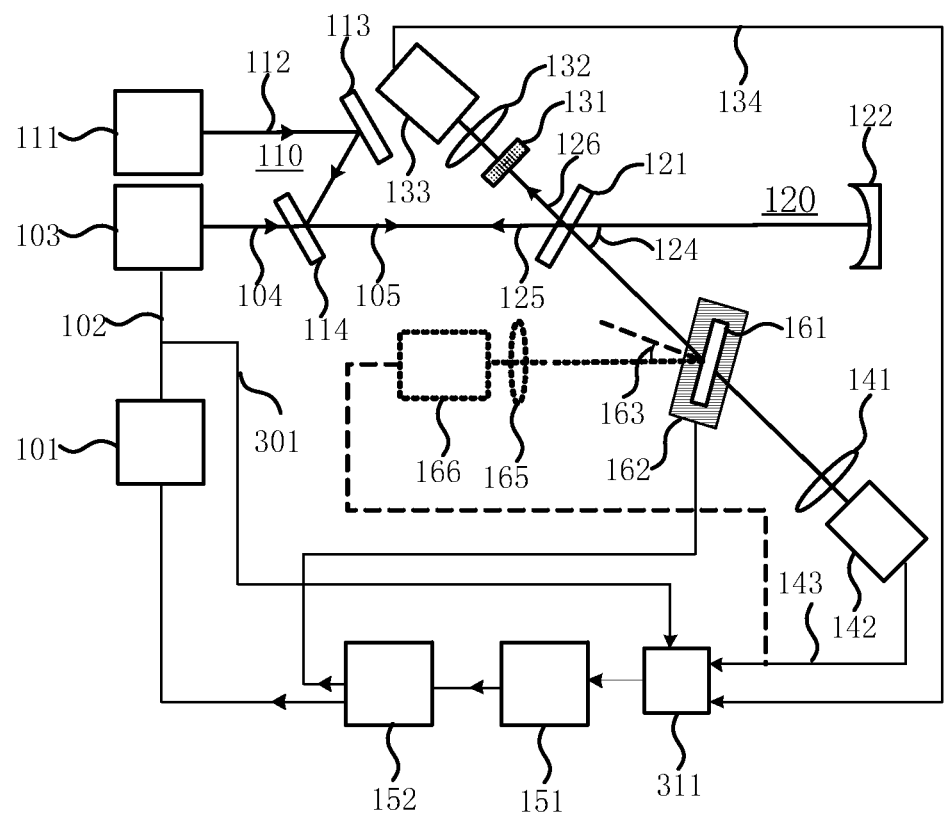

As shown in FIG. 3, in the photometry configuration, in case the electrical signals 134 and 143 from the two photo-detectors 133 and 142 (166) are weak (for example, less than 10 mV), a dual-channel lock-in amplifier 311 is employed to measure the electrical signals 134 and 143, in order to improve the signal-to-noise ratios of the electrical signals. A square-wave electrical signal 301 (that is the same as 102) generated from the function generation unit 101 is used as the reference signal of the lock-in amplifier 311.

Various features of the present technology include: improved measurement accuracy for reflectance higher than 98% as compared to conventional spectrophotometry or ratiometry based techniques; wider measurement dynamic range (from 0 to 99.9999% or more) as compared to conventional CRD techniques; low cost as a broadband CW semiconductor laser (for example an F-P semiconductor laser) can be used as the light source; simple CRD arrangement as elements employed in the conventional CW-CRD schemes, such as optical isolator, PZT, AOS, are eliminated; and easy switching between the CRD apparatus and the photometric apparatus as the switching can be realized by removing or inserting only the output cavity mirror of the CRD apparatus.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:

1. An apparatus for measuring a reflectance of an optical laser component, the apparatus comprising:
a function generation unit configured to generate a square-wave signal;
a semiconductor laser whose excitation current/voltage is modulated by the square-wave signal from the function generation unit;
a beam splitter splitting a laser beam from the semiconductor laser into a reference laser beam and a probe laser beam;
an optical ring-down cavity having at least three mirrors, wherein the optical laser component is placed inside the optical ring-down cavity;
a first detector measuring a power of the probe laser beam exiting the optical ring-down cavity, and transforming the power into a first electrical signal;

a second detector measuring a power of the reference laser beam, and transforming the power into a second electrical signal;

first and second optical lenses or lens sets focusing the probe laser beam and the reference laser beam into the first and second detectors, respectively;

a data acquisition unit acquiring and recording the first and second electrical signals from the first and second detectors; and a computer controlling the function generation unit and data acquisition unit, and processing the first and second electrical signals from the first and second detectors to determine the reflectance of the optical laser component.

2. The apparatus of claim 1, wherein the optical ring-down cavity is optically stable and comprises first and second plano-concave mirrors and a planar mirror, and wherein the concave surfaces of the first and second plano-concave mirrors and one surface of the planar mirror comprise highly-reflective coatings, and wherein the reflectance of the three coated surfaces are higher than 99% and the three coated surfaces form internal walls of the optical ring-down cavity.

3. The apparatus of claim 2, wherein the first and second plano-concave mirrors are on optical axis of the optical ring-down cavity generally perpendicularly, while the planar mirror is placed on optical axis of the optical ring-down cavity obliquely.

4. The apparatus of claim 2, wherein the planar mirror and the first plano-concave mirror form a first arm of the optical ring-down cavity, and wherein the planar mirror and the second plano-concave mirror form a second arm of the optical ring-down cavity.

5. The apparatus of claim 4, wherein the angle between the first and second arms of the optical ring-down cavity is in the range of about 3° to about 150°.

6. The apparatus of claim 1, wherein the beam splitter is configured to transmit the probe laser beam and to reflect the reference laser beam, and the beam splitter is placed between the semiconductor laser and the optical ring-down cavity.

7. The apparatus of claim 6, wherein the beam splitter is also used as the planar mirror of the optical ring-down cavity.

8. The apparatus of claim 1, wherein the first detector and first lens or lens set are proximate the second plano-concave mirror along the second arm of the optical ring-down cavity to detect the power of the probe laser beam.

9. The apparatus of claim 1, wherein the second detector and second lens or lens set are placed to detect the power of the reference laser beam.

10. The apparatus of claim 1, further comprising a variable attenuator between the second detector and the beam splitter.

11. The apparatus of claim 1, wherein a test optical laser component is inserted into the second arm of the optical ring-down cavity to form a test optical cavity which then comprises two plano-concave mirrors, a planar mirror, and the test optical laser component.

12. The apparatus of claim 11, wherein the test optical laser component is placed on a two-dimensional translation stage.

13. The apparatus of claim 1, further comprising a dual-channel lock-in amplifier or two lock-in amplifiers amplifying the electrical signals from the first and second detectors and outputting the amplified electrical signals to the data acquisition unit, so as to improve the signal-to-noise ratios of the electrical signals.

14. A method for measuring reflectance of an optical laser component, the method comprising:
(a) providing an optical ring-down cavity with two plano-concave mirrors and a planar mirror;
(b) directing a probe laser beam into the optical ring-down cavity from the planar mirror, with the probe laser beam being emitted from a semiconductor laser and transmitted through a beam splitter;
(c) measuring and transforming an optical power of a reference laser beam into an electrical signal by a second detector, with the reference laser beam being emitted from the semiconductor laser and reflected by the beam splitter;
(d) measuring and transforming an optical power of the probe laser beam transmitted through the optical ring-down cavity into an electrical signal by a first detector, and recording the electrical signal after switching off the semiconductor laser and determining a decay time of the initial optical ring-down cavity from the measured Cavity Ring-Down (CRD) signal;
(e) removing the output plano-concave mirror of the optical ring-down cavity, measuring and transforming the optical power of the probe laser beam into an electrical signal by the first detector;
(f) inserting a test optical laser component into the optical ring-down cavity to form a test optical ring-down cavity, repeating (b) to (d) to determine a decay time of the test optical ring-down cavity, and measuring and transforming the optical power of the probe laser beam into an electrical signal by the first detector after removing the output plano-concave mirror of the test optical ring-down cavity;
(g) calculating reflectance of the test optical laser component via the decay times of the initial optical ring-down cavity and the test optical ring-down cavity, wherein when the calculated reflectance of the test optical laser component in (g) is lower than 98% or there is no measurable CRD signal in (f), calculating reflectance of the test optical laser component via calculating a ratio of amplitudes of the electrical signals of the first and second detectors and calibrating the ratio.

15. The method of claim 14, wherein the probe laser beam is transmitted through the planar mirror into the optical ring-down cavity on optical axis of the optical ring-down cavity.

16. The method of claim 14, wherein a variable attenuator is used to adjust the power of the reference laser beam.

17. The method of claim 14, wherein an incident angle of the probe laser beam onto the test optical laser component is set to the application angle of incidence of the test optical laser component, which is in a range of about 1° to about 85°.

18. The method of claim 14, wherein the excitation current/voltage of the semiconductor laser is modulated by a square-wave signal with a frequency less than the reciprocal of ten times of the initial optical cavity decay time.

19. The method of claim 14, wherein the test optical laser component is placed on a two-dimensional translation stage for two-dimensional mapping of the reflectance.

20. The method of claim 14, wherein a dual-channel lock-in amplifier or two lock-in amplifiers is/are employed to amplifying the electrical signals from the first and second detectors so as to improve the signal-to-noise ratio of the electrical signals.

* * * * *

UNITED STATES PATENT AND TRADEMARK OFFICE
CERTIFICATE OF CORRECTION

| | | |
|---|---|---|
| PATENT NO. | : 8,456,640 B2 | Page 1 of 1 |
| APPLICATION NO. | : 13/231711 | |
| DATED | : June 4, 2013 | |
| INVENTOR(S) | : Li et al. | |

It is certified that error appears in the above-identified patent and that said Letters Patent is hereby corrected as shown below:

On the Title page, [73] "Institute of Microelectronics, Chinese Academy of Sciences" should read -- Institute of Optics and Electronics, Chinese Academy of Sciences --.

Signed and Sealed this
Eighth Day of April, 2014

Michelle K. Lee
*Deputy Director of the United States Patent and Trademark Office*